US012157899B2

(12) United States Patent
Washburn

(10) Patent No.: US 12,157,899 B2
(45) Date of Patent: Dec. 3, 2024

(54) ACELLULAR PLACENTAL PREPARATIONS

(71) Applicant: PLAKOUS THERAPEUTICS, INC., Winston-Salem, NC (US)

(72) Inventor: Scott A. Washburn, Pfafftown, NC (US)

(73) Assignee: PLAKOUS THERAPEUTICS, INC., Winston-Salem, NC (US)

( * ) Notice: Subject to any disclaimer, the term of this patent is extended or adjusted under 35 U.S.C. 154(b) by 1028 days.

(21) Appl. No.: 16/321,075

(22) PCT Filed: Mar. 14, 2017

(86) PCT No.: PCT/US2017/022257

§ 371 (c)(1),
(2) Date: Jan. 28, 2019

(87) PCT Pub. No.: WO2017/160804

PCT Pub. Date: Sep. 21, 2017

(65) Prior Publication Data

US 2020/0239836 A1 Jul. 30, 2020

Related U.S. Application Data

(60) Provisional application No. 62/307,629, filed on Mar. 14, 2016.

(51) Int. Cl.

| | |
|---|---|
| ***C12N 5/073*** | (2010.01) |
| ***A61K 35/50*** | (2015.01) |
| ***A61K 38/55*** | (2006.01) |

(52) U.S. Cl.
CPC ............ *C12N 5/0605* (2013.01); *A61K 35/50* (2013.01); *A61K 38/55* (2013.01)

(58) Field of Classification Search
None
See application file for complete search history.

(56) References Cited

U.S. PATENT DOCUMENTS

| | | | |
|---|---|---|---|
| 10,960,028 B2 | 3/2021 | Washburn et al. | |
| 11,806,370 B2 | 11/2023 | Washburn et al. | |
| 2003/0235580 A1 | 12/2003 | Zhang | |
| 2007/0071740 A1 | 3/2007 | Tseng et al. | |
| 2007/0071828 A1 | 3/2007 | Tseng et al. | |
| 2008/0181967 A1 | 7/2008 | Liu et al. | |
| 2011/0206776 A1 | 8/2011 | Tom et al. | |
| 2013/0245528 A1 | 9/2013 | Harrell | |
| 2015/0367020 A1 | 12/2015 | Andrews et al. | |
| 2016/0339061 A1* | 11/2016 | Tseng | A61K 35/51 |

FOREIGN PATENT DOCUMENTS

| | | |
|---|---|---|
| CN | 101316602 A | 12/2008 |
| CN | 102327640 | 1/2012 |
| CN | 103114073 | 5/2013 |
| CN | 103861151 | 6/2014 |
| CN | 103520780 | 3/2015 |
| JP | 2014098021 | 5/2014 |
| KR | 20110025266 A | 3/2011 |
| WO | 2008060377 | 5/2008 |
| WO | 2013/082158 | 6/2013 |
| WO | 2015038477 | 3/2015 |
| WO | 2015171142 | 11/2015 |
| WO | 2017160804 | 9/2017 |

OTHER PUBLICATIONS

Varney, Helen; Kriebs, Jan M.; Gegor, Carolyn L, editors. Varney's midwifery. 2004, Boston: Jones and Bartlett Publishers. pp. 543, 564-569. (Year: 2004).*

Sigma-Aldrich (2022) Product information sheet for "P8340 Protease Inhibitor Cocktail" (Year: 2022).*

Sigma-Aldrich (2022) Product information sheet for "04693124001 Roche complete(TM), Mini Protease Inhibitor Cocktail". (Year: 2002).*

Wilshaw et al, Tissue Engineering: Pt A, 2008, vol. 14, No. 4, pp. 463-472. (Year: 2008).*

Ahmed et al, The Journal of Clinical Endocrinology & Metabolism, vol. 85, pp. 755-764 (2000). (Year: 2000).*

"Tissue" definition, Merriam-Webster Online Dictionary, 2022. Retrieved from URL: https://www.merriam-webster.com/dictionary/tissue#:~: text=Definition%20of%20tissue,a%20plant%20or%20an%20animal on Sep. 8, 2022. (Year: 2022).*

Powers et al, Chem Rev, 2002, 102:4639-4750. (Year: 2002).*

"COmplete, Mini," Cat. No. 4 693 124, Roche, 2005, pp. 1-3.

"Report in the Eighteenth Japanese Pharmacopoeia Clinical Practitioner <1> Differences Between Laennec and Melsmon, Action Mechanism of Comcenter," Skin Solution Clinics, 2015, pp. 1-4.

"Protein Purification: Principles, High Resolution Methods, and Applications," 3rd Edition, Janson, J. ed., J. Wiley & Sons, Inc., Mar. 2011, 12 pages.

Koichiro et al., "A Leukocyte Mobilfactor From Human Placental Chorionic Cells (Interleukin-8 (IL-8)), Monocyte Chemotactic Activating Factor (MCAF) Production", vol. 45, 1949, p. 352.

Naruse, K. et al., "Cytokines, Proteases, and Ligands of Receptor for Advanced Glycation Endproducts (Rage) Released by Primary Trophoblasts from Human Term Placenta Under Hypoxic Stimulation," Hypertension Research in Pregnancy, 1(2):81-87 (2013).

Yoshida et al., "A Placenta Therapy and Integrated Medicine", Japanese placenta Tokyo Metropolitan Institute of Medical Science, No. 2, 2008, pp. 30-45.

U.S. Appl. No. 16/480,395, Non-Final Office Action, Aug. 18, 2020, 8 pages.

U.S. Appl. No. 16/480,395, Notice of Allowance, Dec. 2, 2020, 10 pages.

CA 3,016,606, Office Action, Sep. 10, 2020, 4 pages.

CN 201780023893.3, Office Action, Jul. 10, 2020, 19 pages.

CN 201780023893.3, Office Action, Apr. 21, 2021, 9 pages.

EP 17767314.2, Office Action, Aug. 17, 2020, 5 pages.

JP 2018-549193, Office Action, Apr. 22, 2021, 6 pages.

Protease/Phosphatase Inhibitor Cocktail (100X), Cell Signaling Technology, Inc., Available online at: https://media.cellsignal.com/pdf/5872.pdf, Jan. 1, 2014, 1 page.

(Continued)

*Primary Examiner* — Allison M Fox

(74) *Attorney, Agent, or Firm* — Kilpatrick Townsend & Stockton LLP

(57) ABSTRACT

Biological products are disclosed that have improved qualities relative to those that are currently available. Disclosed are compositions and methods for modulating cellular physiology and pathological processing using compositions that are derived from various placenta/villous chorion tissue.

19 Claims, 6 Drawing Sheets

(56) References Cited

OTHER PUBLICATIONS

CA3,016,606 , “Office Action”, Jul. 15, 2019, 3 pages.
EP17767314.2 , “Extended European Search Report”, Sep. 19, 2019, 6 pages.
Kim et al., “Amniotic Membrane Patching Promotes Healing and Inhibits Proteinase Activity on Wound Healing Following Acute Corneal Alkali Burn”, Experimental Eye Research., vol. 70, No. 3, Mar. 1, 2000, pp. 329-337.
PCT/US2017/022257 , “International Preliminary Report on Patentability”, Sep. 27, 2018, 6 pages.
PCT/US2017/022257 , “International Search Report and Written Opinion”, Jun. 8, 2017, 9 pages.
PCT/US2018/016383 , “International Preliminary Report on Patentability”, Aug. 15, 2019, 8 pages.
PCT/US2018/016383 , “International Search Report and Written Opinion”, May 17, 2018, 12 pages.
“Protease Phosphatase Inhibitor Cocktail (100X)”, Cellsignal.com, Available Online at: https://media.cellsignal.com/pdf/5872.pdf, Jan. 1, 2014, 1 page.
Kawakatsu et al., “Placental Extract Protects Bone Marrow-Derived Stem/Progenitor Cells Against Radiation Injury Through Anti-Inflammatory Activity”, Journal Of Radiation Research, vol. 54, No. 2, Mar. 1, 2013, pp. 268-276.
Kim et al., “Protective Effects Of Human Placenta Extract On Cartilage Degradation In Experimental Osteoarthritis”, Biological & Pharmaceutical Bulletin , vol. 33, No. 6, Jan. 1, 2010, pp. 1004-1010.
Kong et al., “Effect Of Human Placental Extract On Health Status In Elderly Koreans”, Evidence-Based Complementary And Alternative Medicine, vol. 2012, Jan. 1, 2012, pp. 1-6.
AU 2017235220, Notice of Acceptance, Mar. 9, 2022, 3 pages.
EP 21198147.7, Extended European Search Report, Apr. 26, 2022, 12 pages.
JP 2018-549193, Notice of Decision to Grant, Mar. 1, 2022, 4 pages.
IN 201817034213, First Examination Report, Jun. 7, 2022, 8 pages.
AU 2017235220, First Examination Report, Oct. 30, 2021, 4 pages.
CA 3,016,606, Office Action, Oct. 15, 2021, 5 pages.
CN 201780023893.3, Notice of Decision to Grant, Nov. 8, 2021, 2 pages.
EP 17767314.2, Notice of Decision to Grant, Nov. 25, 2021, 2 pages.
English Machine Translation of Chinese publication 103861151 A mailed on Jun. 18, 2014, 9 pages.
U.S. Appl. No. 17/214,144, Corrected Notice of Allowability mailed on Sep. 18, 2023, 3 pages.
U.S. Appl. No. 17/214,144, Notice of Allowance mailed on Jun. 12, 2023, 12 pages.
Australian Application No. 2022204044, First Examination Report mailed on Aug. 7, 2023, 4 pages.
Canadian Application No. 3,016,606, Office Action mailed on Jan. 20, 2023, 5 pages.
Chinese Application No. 202210069029.X, Office Action mailed on Aug. 26, 2023, 13 pages (9 pages of Original Document and 4 page of English Translation).
European Application No. 21198147.7, Office Action mailed on Apr. 28, 2023, 4 pages.
Japanese Application No. 2022-052707, Office Action mailed on May 30, 2023, 7 pages.
Mihee et al., Effect of Human Placental Extract on Health Status in Elderly Koreans, Evidence-Based Complementary and Alternative Medicine, vol. 2012, 2012, pp. 1-5.
Schweizer, Amniotic Membrane of the Placenta—Part 1, Parent’s Guide to Cord Blood Foundation Available Online at: https://parentsguidecordblood.org/en/news/amniotic-membrane-placenta-part-1, Sep. 2016, pp. 1-5.
JP2022-052707 , “Office Action”, Nov. 14, 2023, 3 pages.
AU2022204044 , “Notice of Acceptance”, Feb. 22, 2024, 3 pages.
CN202210069029.X , “Office Action”, Jan. 18, 2024, 8 pages.

* cited by examiner

ACELLULAR PLACENTAL PREPARATIONS

CROSS-REFERENCES TO RELATED APPLICATIONS

This application is a U.S. national phase of International Application PCT/US2017/022257 filed Mar. 14, 2017, which claims priority to U.S. Provisional Application No. 62/307,629, filed on Mar. 14, 2016, each of which is incorporated herein by reference in its entirety.

FIELD

Described herein are biological compositions, methods of making compositions, and methods of using compositions. In embodiments, a composition is derived from placenta tissue.

BACKGROUND

The human placenta connects the fetus to the mother's uterine wall and is responsible for the protection and development of the fetus effectively from conception to the time of birth.

SUMMARY

The present invention relates to compositions and associated methods of preparing and using placental tissue products/compositions. Placental tissue includes the placental disc and the amniotic sac. The amniotic sac comprises two primary layers, the chorion and the amnion.

In an embodiment, the composition described herein comprises protease inhibitors. In some embodiments, protease inhibitors may be added to placental tissue during the purification process and may not be removed.

In certain embodiments, the placental tissue is processed to isolate desirable proteins and chemokines from the placental tissue. In an embodiment of the present invention, a method comprising adding protease inhibitors to a placental product and then administering one or more of gross homogenization and cell lysis. In some embodiments, the method further comprises separation of fluid from solid cell components, filtration, lyophilization and/or freezing.

In certain embodiments, compositions described herein may be used in the treatment of arthritis, wound healing, scar treatment, tissue growth and healing, tissue matrix regeneration and repair, engraftment, inflammation, conditions associated with modulating TGF-β, and/or other protein signaling.

The composition and methods of the present invention may be desirable because of elevated concentrations of proteins relative to conventional compositions that do not use protease inhibitors.

DETAILED DESCRIPTION OF THE INVENTION

Figure 1:
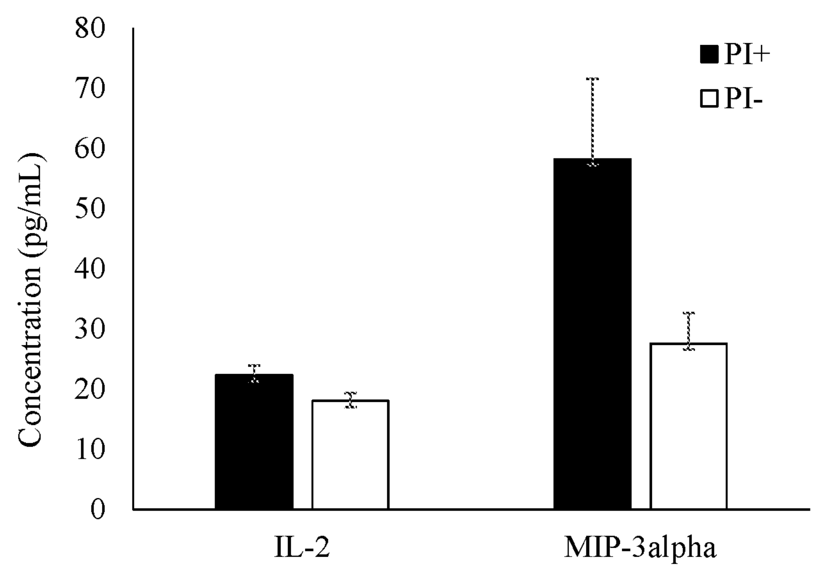
FIG. 1 shows the protein concentration amounts of interleukin 2 and macrophage inflammatory protein 3 from placental tissue in both the presence and absence of protease inhibitors.

The present invention relates to compositions and associated methods of preparing placental tissue products/compositions. The human placenta connects the fetus to the mother's uterine wall and is responsible for the protection and development of the fetus effectively from conception to the time of birth. During pregnancy, the placenta helps the fetus develop by providing nutrients and oxygen, by performing some immunity functions, and by releasing growth factors and cytokines, small proteins that act to direct cell migration.

During pregnancy, the placenta provides nutrients, growth factors, and cytokines to the fetus via the umbilical cord and amniotic fluid. Both the fetus and placenta express antigens that are disparate from the mother, yet avoid being rejected by the maternal immune system during the pregnancy. The residual cells, transport properties, and limited immune response of placental tissue help make it desirable and/or advantageous to utilize placental tissue in medical applications.

Placental tissue may be typically collected after an elective Cesarean surgery. Placental tissue may also be collected after a normal vaginal delivery. The tissue may be used unmodified in some applications. However, it would be advantageous to improve the performance of placental tissue for enhanced medical applications. For example, it is advantageous and/or desirable to isolate placental tissue proteins, growth factors, and chemokines for various medical applications.

For purposes of describing certain embodiments of the present invention, reference is made herein to human placenta tissue. Embodiments of the present invention, however, are not limited to comprising naturally occurring human placenta tissue. Embodiments of the present invention may include, but are not limited to: natural or synthetic human placenta tissue; natural or synthetic mammalian placenta tissue; natural or synthetic placenta tissue from other animals, e.g., bovine, equine, porcine, ovis, capra, or camelid; and/or natural and/or synthetic compositions having similar properties to placenta tissue.

Placenta tissue comprises the placental disc, the amniotic sac, and umbilical cord, its vessels and Wharton's Jelly cushioning the umbilical cord vessels. The amniotic sac comprises the outer chorion and the inner amnion. The chorion comprises a reticular layer, basement layer, and trophoblast layer. The trophoblast layer may be adhered to the maternal decidua. The umbilical cord connects the placenta to the fetus, and may transport oxygenated blood and nutrients to the fetus. Much of the placental disc is comprised of chorionic villi, which are extensions of the chorionic villous tree. Through these structures, fetal nutrition and exchange of fetal and maternal cytokines and growth factors may occur.

Placenta villi are composed of three layers of components with different cell types in each: (1) syncytiotrophoblasts/cytotrophoblasts that may cover the entire surface of the villous tree and bathe in maternal blood within the intervillous space; (2) mesenchymal cells, mesenchymal derived macrophages (Hofbauer cells), and fibroblasts that may be located within villous core stroma between trophoblasts and fetal vessels; and (3) fetal vascular cells that include vascular smooth muscle cells, perivascular cells (pericytes), and endothelial cells. Hofbauer cells may synthesize VEGF and other proangiogenic factors that initiate vasculogenesis in the placenta.

Both the fetus and placenta may express antigens that are disparate from the mother, yet avoid being rejected by the maternal immune system during the pregnancy. The limited immuno response of the placental tissue is believed to assist the placenta in avoiding fetal rejection during pregnancy.

The transport properties, residual cells, and limited immune response of placental tissue help make it desirable to utilize placental tissue in medical applications. Placental tissue may be collected after an elective Cesarean surgery. Placental tissue may also be collected after a normal vaginal delivery. Placental tissue may be obtained through FDA registered tissue banks. The tissue may be used unmodified in some applications. However, it would be advantageous to improve the performance of the placental tissue for enhanced medical applications.

The placental products/compositions described herein may have beneficial properties relative to those placental preparations of the prior art. For example, the placental products/compositions of the present invention include protease inhibitors that are added to placental tissue during the purification process and are not removed. The methods of the invention include the treatment of arthritis, wound healing, scar treatment, tissue growth and healing, engraftment, inflammation, and conditions associated with modulating TGF-β and other protein signaling.

To date, various preparations have been purified from the placenta that have been used for a variety of purposes such as treating inflammation, scar treatment, modulating TGF-β signaling, treating apoptosis and associated conditions. However, because governmental regulatory agencies may require more stringent testing conditions and more extensive clinical trials when foreign additives are added to preparations (such as additives to various amniotic or placental preparations), those of skill in the art have been reluctant to include these additives to purified preparations due to the added cost, added regulatory requirements, as well as other factors. However, the preparations created by others that have failed to include and/or contemplate including these additives have also unfortunately failed to unlock the true potential value/uses of these preparations. It is with these shortcomings in mind that the present invention was developed.

Placental Compositions

In embodiments, the present invention relates to placental tissue products and compositions. Placental tissue as used herein comprises chorion frondosum tissue, decidua basalis tissue, and/or interconnecting tissue, which may be in whole or in part. In some embodiments, compositions described herein have beneficial properties relative to conventional placental preparations of the prior art. For example, in some embodiments, the placental products/compositions described herein comprise protease inhibitors that are added to placental tissue during the purification process. In some embodiments, the protease inhibitors may remain in the placental product.

In an embodiment, the protease inhibitors may be removed prior to using the placental product to treat an individual that suffers from various conditions, including arthritis, wound healing, scar treatment, tissue growth and healing, engraftment, inflammation, and conditions associated with modulating TGF-β and other protein signaling. For example, by employing a column that has antibodies that specifically bind the protease inhibitors, the protease inhibitors may be removed prior to treatment of said individual. As used herein, the terms maladies, diseases, and conditions may be used interchangeably.

In an embodiment, the present invention relates to purified compositions and placenta/villous chorion preparations i.e., compositions that may be prepared from placenta/villous chorion materials. In some embodiments, at least one component of the purified compositions may be obtained from placenta/villous chorion preparations. In some embodiments, the present invention also relates to purified compositions in which at least one component of the purified composition may be obtained from human placenta and chorion. In an embodiment, the present invention relates to methods for preparing any of the purified compositions and preparations described herein. The present invention also relates to methods for storing and preserving any of the aforementioned purified compositions and preparations. Further, the present invention relates to methods for using the aforementioned purified compositions and preparations, including preservative methods, cell culture methods, tissue culture methods, therapeutic methods, prophylactic methods and cosmetic methods.

In an embodiment, methods for reducing or preventing inflammation in a subject comprise providing an effective amount of an inflammation inhibition composition to a subject in need of inflammation inhibition or prevention, where the composition comprises at least one human amniotic material selected from a human amniotic membrane, a human amniotic jelly, a human amniotic stroma, placenta/villous chorion or a combination thereof extracted from a placenta. In some embodiments, the material may be extracted from the human amniotic material. In some embodiments, the composition may comprise, for example, cross-linked high molecular weight hyaluronan (HA), Tumor necrosis factor-stimulated gene 6 (TSG-6), Pentraxin (PTX-3), and Thrombospondin (TSP-1).

In some embodiments, the extraction method may comprise, obtaining a human placenta, isolating the human amniotic material from the placenta, and homogenizing the human amniotic material in a suitable buffer. In some embodiments, a frozen or previously-frozen human placenta may be used. If the placenta is frozen, the procedure may comprise thawing the placenta prior to isolating the human amniotic material from the thawed placenta. Optionally the method may further comprise lyophilizing the homogenate to a powder. Optionally, the method may comprise admixing the homogenate or the powder with a pharmaceutically acceptable carrier for a non-solid dosage form or an extended release solid dosage form. In an embodiment, the preparation procedure may substitute the step of lyophilizing the homogenate with the step of centrifuging the homogenate, isolating the supernatant from the centrifuged homogenate, and optionally lyophilizing the supernatant to a powder. In an embodiment, one may alternatively or additionally freeze the centrifuged homogenate. In some embodiments, the composition may be provided as a non-solid dosage form or an extended release solid dosage form.

In an embodiment, the present invention relates to adding protease inhibitors to a placental preparation prior to undergoing any of purification steps described herein of the placental preparation. In an embodiment, the protease inhibitors may remain in the placental preparation throughout the entire purification protocol. In some embodiments, the protease inhibitors may remain in the placental preparation that has been purified when the purified product is used for one of the disclosed methods herein. In an embodiment, the protease inhibitors may be added to live cells and/or live tissues when undergoing the purification protocol.

In one embodiment, the present invention relates to a cell free composition that comprises one or more of growth factors and/or cytokines derived from placental origin, where said composition comprises at least one protease inhibitor.

In an embodiment, the protease inhibitor may be one of more inhibitors that inhibit serine proteases, cysteine proteases, metalloproteases, aspartic proteases, threonine proteases, or trypsin inhibitors. In some embodiments, the one or more protease inhibitors may inhibit all of serine proteases, cysteine proteases, metalloproteases, aspartic proteases, threonine proteases, and trypsin inhibitors. In some embodiments, the protease inhibitors may inhibit serine proteases and cysteine proteases.

In one embodiment, protease inhibitors that may be used in the present invention include one or more 4-(2-Aminoethyl) benzenesulfonyl fluoride hydrochloride (AEBSF), Bovine Lung Aprotinin, N-(trans-Epoxysuccinyl)-L-leucine 4-guanidinobutylamide, and Leupeptin. In an embodiment, other protease inhibitors that may be used include N-ethylmaleimide (NEM), phenylmethylsulfonylfluoride (PMSF), ethylenediamine tetraacetic acid (EDTA), ethylene glycol-bis-(2-aminoethyl(ether)NNN'N'-tetraacetic acid, ammonium chloride, boceprevir, danoprevir, narlaprevir, telaprevir, or vaniprevir.

In an embodiment, the placental composition may be derived from tissues and/or cells from any one or more of the chorion, the placenta, the amnionic sheet, the amnion, the umbilical cord, the mesoderm, the yolk sac, the exocoelem, Hofbauer cells, endothelial cells, and/or the endoderm. In one embodiment, the purified placental composition derives from cells and/or tissue from the chorion that has had protease inhibitors added to it prior to any purification steps. In one embodiment, the protease inhibitors that may be added include 4-(2-Aminoethyl) benzenesulfonyl fluoride hydrochloride (AEBSF), Bovine Lung Aprotinin, N-(trans-poxysuccinyl)-L-leucine 4-guanidinobutylamide, and Leupeptin. It has been found that when the chorion is used as the starting material in the purification process, that a more uniform purification product may be attained.

Method of Purifying Compositions

In an embodiment, the present invention relates to a cell free preparation that may preserve the proteins both from the extracellular matrix and intracellular compartments of the placenta. In one embodiment, the present invention relates to a cell free preparation that may preserve the proteins found in the trophoblastic cells. In an embodiment, the invention relates to a cell free preparation that may preserve the proteins in the cytotrophoblasts, which may synthesize the various cytokines and growth factors for fetal development. Alternatively and/or additionally, the present invention relates to a cell free preparation that may preserve the proteins found in the syncytiotrophoblasts, which are pseudocells that may store products of cytotrophoblasts. The syncytiotrophoblast is a multinuclear layer that may form and expand throughout pregnancy by intercellular fusion of the underlying feeder layer of mononuclear villous cytotrophoblasts.

In one embodiment, by adding protease inhibitors throughout the purification process and keeping them as part of the composition, one may be able to isolate compositions having significantly elevated concentrations of proteins relative to those preparations where protease inhibitors are not used. For example, in an embodiment, at least one of the following proteins can be found at elevated levels relative to those purification methods where protease inhibitors are not used: granulocyte chemotactic protein 2 (GCP-2), interleukin 2 (IL-2), interleukin 8 (IL-8), monocyte chemotactic protein 1 (MCP-1), macrophage inhibitory factor (MIF), macrophage inflammatory protein 1 (MEP-1α), and macrophage inflammatory protein 3 (MIP-3α). In some embodiments, several of these proteins are found at elevated concentrations. In some embodiments, all of these proteins are found at elevated concentrations relative to those preparations/compositions that are performed in the absence of protease inhibitors.

In some embodiments, the purification protein concentration may match the cytokines and growth factors that are present in the chorion at the 16th week of human gestation. In an embodiment, the isolated composition may show superior properties compared to conventional preparations/compositions that do not use protease inhibitors. For example, wound healing in the preparations/compositions using the methods of the present invention may be unexpectedly superior to compositions isolated without using protease inhibitors.

In some embodiments, the method of purifying the composition may comprise a number of purification steps. In some embodiments, the method of purification may comprise homogenization and cell lysis. In some embodiments, the methods of purification may further comprise tissue isolation. In some embodiments, the placenta may be pretreated to isolate the tissue by removing excess amounts of blood from the tissue. For example, the placenta, which may be stored in a normal saline solution awaiting processing may be placed in a container with a buffered solution, such as phosphate buffered saline solution (PBS), and mixed to remove excess blood. In some embodiments, the container of tissue in solution may be sonicated, placed on a shaking platform, or agitated. In some embodiments, placenta pieces may be grossly homogenized using a laboratory blender or similar means. Optionally, the pieces may be homogenized with 1×PBS comprising protease inhibitor (PI). In some embodiments, the PI may be at a 1× final concentration. Not intending to be bound by theory, the protease inhibitor may prevent the breakdown of proteins, specifically growth factors, chemokines, and cytokines present in the cells of the placenta.

In some embodiments, the homogenized solution may be separated to remove excess blood liberated during homogenization process. In some embodiments, the separation may be performed by filtration or centrifugation, where the fluid may be discarded and the solids retained for further processing. The solids may compact during centrifugation, forming a mass at the bottom of the container. In some embodiments, the solids may be washed or more times to further remove excess blood from the homogenized solids.

Optionally, the washed solids may be cooled prior to further processing. In some embodiments, the washed solids may be cooled to less than 10° C.

In some embodiments, cell lysis may be performed by various methods, including but not limited to, high pressure homogenization, freeze/thaw, chemical, sonication, osmotic pressure, high shear mixing, or combinations thereof. Not intending to be bound by theory, cell lysis may release chemokines, cytokines, and growth factors from the cells. In some embodiments, the lysed cells or cellular debris may be separated from fluid. The fluid or supernatant may comprise chemokines, cytokines, and growth factors and in some embodiments, may be retained for further processing.

In some embodiments, the method of purification may further comprise tissue dissection prior to homogenization. The optional dissection may increase the efficiency of the homogenization process. The dissection may also allow for increased methods to be used for homogenization, without a size on tissue feed. As one example, the tissue may be cut into smaller pieces, such as 2 inches by 2 inches.

In some embodiments, the method of purification may further comprise separation of fluid from solid cell components, for example by filtration or centrifugation. In some embodiments, the method of purification may further comprise lyophilization and/or freezing or some other purification protocol. In some embodiments, the human placental homogenate (HPH) preparations may be preserved by lyophilization placing in sterile vials, placing in sterile vials in liquid form for later use, spray drying, or other methods known by one skilled in the art. In some embodiments, the HPH may be added to other placental products.

In some embodiments, the purification steps may comprise: (1) tissue isolation; (2) homogenization; (3) cell lysis; (4) separation of fluid from solid cell components; and (5) lyophilization and/or freezing or some other purification protocol.

In some embodiments, the protease inhibitors may be added after the tissue has been isolated. In some embodiments, the protease inhibitors may be present during cell lysis. In an embodiment, the protease inhibitors may be present throughout the full purification of the composition, including when the composition may be used in the methods described herein.

Compositions for Pharmaceutical Use

In an embodiment, the present invention relates to generating pharmaceutical compositions. In some embodiments, the pharmaceutical composition may contain pharmaceutically acceptable salts, solvates, and products thereof, and may contain diluents, excipients, carriers, or other substances necessary to increase the bioavailability or extend the lifetime of the ingredients/compounds of the present invention.

In some embodiments, subjects that may be treated by the ingredients/compounds and compositions of the present invention include, but are not limited to, horses, cows, sheep, pigs, mice, dogs, cats, primates such as chimpanzees, gorillas, rhesus monkeys, and humans. In an embodiment, a subject may be a human in need of cancer treatment.

The pharmaceutical compositions containing the ingredients/compounds of the invention may be in a form suitable for injection either by itself or alternatively, using liposomes, micelles, and/or nanospheres. Alternatively, in some embodiments, the pharmaceutical compositions may be in a form that allows it to be administered topically.

Alternatively, in some embodiments, compositions intended for injection may be prepared according to any known method, and such compositions may comprise one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

In some embodiments, the composition may be aqueous suspensions comprising the active placental ingredients in an admixture with excipients suitable for the manufacture of aqueous suspensions. Such excipients may comprise suspending agents and/or dispersing/wetting agents. Suspending agents may include, for example, sodium carboxymethylcellulose, methylcellulose, hydroxypropylmethylcellulose, sodium alginate, polyvinylpyrrolidone, gum tragacanth and gum acacia. Dispersing or wetting agents may be a naturally-occurring phosphatide, such as lecithin, or a synthesized condensation product, such as condensation products of an alkylene oxide with fatty acids, for example, polyoxyethylene stearate, condensation products of ethylene oxide with long chain aliphatic alcohols, for example, heptadecaethyl eneoxycethanol, condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example, polyethylene sorbitan monooleate. In some embodiments, the aqueous suspensions may also contain one or more coloring agents.

In some embodiments, oily suspensions may be formulated by suspending the active ingredient in a vegetable oil, for example, arachis oil, olive oil, sesame oil or coconut oil, or in a mineral oil such as a liquid paraffin. The oily suspensions may comprise a thickening agent, for example, beeswax, hard paraffin or cetyl alcohol. In some embodiments, sweetening agents and flavoring agents may be added to provide a palatable oral preparation. In some embodiments, these compositions may be preserved by the addition of an anti-oxidant such as ascorbic acid.

In some embodiments, dispersible powders and granules suitable for preparation of an aqueous suspension by the addition of water may provide the active ingredients in admixture with a dispersing or wetting agent, suspending agent and one or more preservatives. Suitable dispersing or wetting agents and suspending agents are exemplified by those already mentioned above. In some embodiments, additional excipients, for example, sweetening, flavoring, and coloring agents may also be present.

In some embodiments, the pharmaceutical compositions of the invention may also be in the form of oil-in-water emulsions. The oily phase may comprise a vegetable oil, for example, olive oil or arachis oil, a mineral oil, for example, a liquid paraffin, or a mixture thereof. Optionally, suitable emulsifying agents may be naturally-occurring gums, for example, gum acacia or gum tragacanth, naturally-occurring phosphatides, for example, soy bean, lecithin, and esters, partial esters derived from fatty acids and hexitol anhydrides, for example, sorbitan monooleate, or condensation products of said partial esters with ethylene oxide, for example, polyoxyethylene sorbitan monooleate. In some embodiments, the pharmaceutical compositions may be in the form of a sterile injectable aqueous or oleaginous suspension. This suspension may be formulated according to the known methods using suitable dispersing or wetting agents and suspending agents described above. Optionally, the sterile injectable preparation may also be a sterile injectable solution or suspension in a non-toxic parenterally-acceptable diluent or solvent, for example, as a solution in 1,3-butanediol. In some embodiments, among the acceptable vehicles and solvents that may be employed are water, sterile water for injection (SWFI), Ringer's solution, and isotonic sodium chloride solution. In addition, sterile, in some embodiments, fixed oils may be conveniently employed as solvent or suspending medium. For this purpose, any bland fixed oil may be employed using synthetic mono- or diglycerides. In addition, in some embodiments, fatty acids such as oleic acid may be used in the preparation of injectables.

In some embodiments, a solution of the invention may be provided in a sealed container, especially one made of glass, either in a unit dosage form or in a multiple dosage form.

In some embodiments, any pharmaceutically acceptable salt of the ingredients of the present invention may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the ingredients of the invention may be a hydrochloric acid salt including a mono, di, or trihydrochloride.

In some embodiments, the composition may also comprise one or more additional components such as a co-solubilizing agent, which may be the same as a solvent, a tonicity adjustment agent, a stabilizing agent, a preservative, or mixtures thereof. Examples of solvents, co-solubilizing agents, tonicity adjustment agents, stabilizing agents and preservatives which may suitable for a solution formulation are described below.

In some embodiments, suitable solvents and co-solubilizing agents may include, but are not limited to, water; sterile water for injection (SWFI); physiological saline; alcohols, e.g., ethanol, benzyl alcohol and the like; glycols and polyalcohols, e.g., propyleneglycol, glycerin and the like; esters of polyalcohols, e.g., diacetine, triacetine and the like; polyglycols and polyethers, e.g., polyethyleneglycol 400, propyleneglycol methylethers and the like; dioxolanes, e.g., isopropylidenglycerin and the like; dimethylisosorbide; pyrrolidone derivatives, e.g., 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™. Suitable tonicity adjustment agents may include, but are not limited to, pharmaceutically acceptable inorganic chlorides, e.g., sodium chloride; dextrose; lactose; mannitol; sorbitol and the like.

In some embodiments, preservatives suitable for physiological administration may be, for example, esters of parahydroxybenzoic acid, e.g., methyl, ethyl, propyl and butyl esters, or mixtures of them, chlorocresol and the like.

In some embodiments, suitable stabilizing agents include, but are not limited to, monosaccharides, e.g., galactose, fructose, and fucose, disaccharides, e.g., lactose, polysaccharides, e.g., dextran, cyclic oligosaccharides, e.g., alpha-, beta-, gamma-cyclodextrin, aliphatic polyols, e.g., mannitol, sorbitol, and thioglycerol, cyclic polyols, e.g., inositol, and organic solvents, e.g., ethyl alcohol and glycerol.

In some embodiments, the above-mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise the compositions described herein or pharmaceutically acceptable salts thereof, and an agent selected from the group consisting of sodium chloride solution (i.e., physiological saline), dextrose, mannitol, or sorbitol, wherein the agent is in an amount of less than or equal to 5%. In some embodiments, the pH of such a formulation may also be adjusted to improve the storage stability using a pharmaceutically acceptable acid or base.

In some embodiments, the concentration of active placental ingredients in the formulation or a pharmaceutically acceptable salt thereof may be less than 100 mg/mL. For example, the concentration may be less than 100 mg/mL, may be less than 75 mg/mL, less than 50 mg/mL, less than 10 mg/mL, or less than 10 mg/mL and greater than 0.01 mg/mL, or between 0.5 mg/mL and 5 mg/mL, or between 1 mg/mL and 3 mg/mL. In an embodiment, the concentration that is used may be the ideal concentration to sufficiently treat the disease and/or condition that is being treated.

In some embodiments, for solution formulations, various compositions of the present invention may be more soluble or stable for longer periods in solutions at a pH lower than 6. Further, in some embodiments, acid salts of the ingredients in the compositions of the present invention may be more soluble in aqueous solutions than their free base counter parts, but when the acid salts are added to aqueous solutions the pH of the solution may be too low to be suitable for administration. Thus, in some embodiments, solution formulations having a pH above pH 4.5 may be combined prior to administration with a diluent solution of pH greater than 7 such that the pH of the combination formulation administered may be pH 4.5 or higher. In one embodiment, the diluent solution comprises a pharmaceutically acceptable base such as sodium hydroxide. In another embodiment, the diluent solution may be at pH of between 10 and 12. In another embodiment, the pH of the combined formulation administered may be greater than 5.0. In another embodiment, the pH of the combined formulation administered may be between pH 5.0 and 7.0.

In some embodiments, the compositions described herein may be passed through a filter. Optionally, one or more additional components such as co-solubilizing agents, tonicity adjustment agents, stabilizing agents and preservatives, for instance of the kind previously specified, may be added to the solution prior to passing the compositions through a sterilizing filter.

Methods of Using the Composition

In some embodiments, the compositions described herein may be used in combination therapy with other compositions that are known to be used on the diseases and/or conditions that the present invention is designed to address. The dosages of the co-administered compounds/compositions may vary depending on the type of co-drug employed, on the specific drug employed, on the disease or condition being treated and so forth. In addition, in some embodiments, when co-administered with one or more biologically active agents, the compounds/compositions provided therein may be administered either simultaneously with the biologically active agent(s) of the present invention or may be administered sequentially. If administered sequentially, the attending physician may determine the appropriate sequence of administering protein in combination with the biologically active agent(s).

In an embodiment, multiple therapeutic agents may be administered in any order or even simultaneously. If administered simultaneously, the multiple therapeutic agents may be provided in a single, unified form, or in multiple forms (by way of example only, either as a single pill or as two separate pills). Optionally, one of the therapeutic agents may be given in multiple doses, or both may be given as multiple doses. If not simultaneous, the timing between the multiple doses may vary from more than zero weeks to less than four weeks. In addition, in some embodiments, the combination methods, compositions and formulations are not to be limited to the use of only two agents; the use of multiple therapeutic combinations may also be envisioned.

In an embodiment, pharmaceutical agents which comprise the combination therapy disclosed herein may be a combined dosage form or in separate dosage forms intended for substantially simultaneous administration. Optionally, the pharmaceutical agents comprising the combination therapy may also be administered sequentially, with either therapeutic compound being administered by a regimen calling for two-step administration. In some embodiments, the two-step administration regimen may call for sequential administration of the active agents or spaced-apart administration of the separate active agents. In some embodiments, the time period between the multiple administration steps may range from, a few minutes to several hours, depending upon the properties of each pharmaceutical agent, such as potency, solubility, bioavailability, plasma half-life and kinetic profile of the pharmaceutical agent.

Moreover, the compositions of the present invention and purified compositions described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics may be combined with genetic testing to determine whether that individual is a carrier of a mutant gene that is known to be correlated with certain diseases or conditions.

The compositions of the present invention described herein and combination therapies may be administered before, during or after the occurrence of a disease or condition, and the timing of administering the composition containing one or more active ingredients may vary. Thus, for example, the compounds may be used as a prophylactic and may be administered continuously to subjects with a propensity to develop conditions or diseases in order to prevent the occurrence of the disease or condition. In some embodiments, the formulations and compositions of the present invention can be administered to a subject during or as soon as possible after the onset of the symptoms. For example, the administration of the formulations and compositions may be initiated within the first 48 hours of the onset of the symptoms, or within the first 48 hours of the onset of the symptoms, or within the first 6 hours of the onset of the symptoms, or within 3 hours of the onset of the symptoms. In some embodiments, the initial administration may be via any route practical, such as, for example, an intravenous injection, a bolus injection, infusion over 5 minutes to about 5 hours, a pill, a capsule, transdermal patch, buccal delivery, topical administration and the like, or any combination thereof. In some embodiments, the formulations and compositions may be administered as soon as is practicable after the onset of a disease or condition is detected or suspected, and for a length of time necessary for the treatment of the disease, such as, for example, from about 1 month to about 3 months. The length of treatment can vary for each subject, and the length may be determined using the known criteria. For example, the compositions containing ingredients that treat the disease or condition may be administered for at least 2 weeks, or about 1 month to about 5 years, or from about 1 month to about 3 years.

The present invention also relates to using the compositions and formulations of the present invention in kits that may be used to treat diseases and conditions that require treatment. In some embodiments, such kits can include a carrier, package, or container that may be compartmentalized to receive one or more containers such as vials, tubes, and the like. Optionally, each of the container(s) may include one of the separate elements to be used in a method described herein. Suitable containers may include, for example, bottles, vials, syringes, and test tubes. The containers may be formed from a variety of materials such as glass or plastic.

In some embodiments, the articles of manufacture provided herein may contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compositions provided herein may be contemplated as are a variety of treatments for any disease, disorder, or condition.

Various methods of use may be contemplated in the present invention. Included in the methods are methods of making and using the placental preparations of the instant invention including the treatment of individuals that are in need of said treatment.

Placental Preparation

In an embodiment, the present invention relates to a placental preparation wherein said placental preparation may be derived from a placental tissue, where the placental tissue may be subjected to processing steps comprising gross homogenization and cell lysis. In some embodiments, the placental tissue may be subjected to processing steps further comprising separation of fluid from solid cell components, filtration, and lyophilization and/or freeze to generate the placental preparation. In some embodiments, the placental preparation further comprises one or more protease inhibitors. In some embodiments, the placental preparation may be derived from placental tissue, where the placental tissue has undergone the following steps in the order of: (a) homogenization; (b) cell lysis; (c) separation of fluid from solid cell components; and (d) lyophilization and/or freeze to generate the placental preparation, where the placental preparation further comprises one or more protease inhibitors. In some embodiments, the preparation may be filtered after the separation and before the lyophilization steps.

In some embodiments, the placental preparation comprises adding the one or more protease inhibitors prior to gross homogenization. In some embodiments, the one or more protease inhibitors comprise one or more of 4-(2-Aminoethyl) benzenesulfonyl fluoride hydrochloride (AEB SF), Bovine Lung Aprotinin, N-(trans-Epoxysuccinyl)-L-leucine 4-guanidinobutylamide, and Leupeptin. Optionally, the one or more protease inhibitors may be selected from the group consisting of 4-(2-Aminoethyl) benzenesulfonyl fluoride hydrochloride (AEB SF), Bovine Lung Aprotinin, N-(trans-Epoxysuccinyl)-L-leucine 4-guanidinobutylamide, and Leupeptin.

In some embodiments, the placental tissue may be the chorion. In some embodiments, the placental preparation may further comprise diluents, excipients, or carriers. In some embodiments, the placental preparation may comprise higher concentration amounts of interleukins relative to preparations that are prepared in the absence of protease inhibitors. In some embodiments, other proteins present in the preparation comprising protease inhibitors may be isolated in higher concentrations relative to proteins in the preparation that are isolated in the absence of protease inhibitors. In some embodiments, the protease inhibitors may not be removed from the placental preparation.

In an embodiment, the present invention relates to a method of treating an individual that may have a malady selected from the group comprising arthritis, wound healing, scar treatment, tissue growth, tissue healing, tissue matrix regeneration/repair, engraftment, inflammation, and conditions associated with modulating TGF-β signaling wherein the method comprises administering the placental preparation as enumerated herein. Tissue is used herein in accordance with its generally accepted meaning in biology, i.e. an ensemble of similar cells. Specific tissues include, but are not limited to, muscle, nerve, bony, connective, epithelial, vascular, and the like.

In an embodiment, the present invention relates to a method of treating an individual that may have a malady selected from the group comprising arthritis, wound healing, scar treatment, tissue growth, tissue healing, tissue matrix regeneration/repair, engraftment, inflammation, and conditions associated with modulating TGF-β and other protein signaling wherein said method comprises administering to said individual an effective amount of a placental preparation that may be derived from placental tissue, where the placental tissue may be subjected to processing steps comprising gross homogenization and cell lysis. In some embodiments, the processing steps may further comprise separation of fluid from solid cell components, filtration, and lyophilization and/or freeze to generate the placental preparation. In some embodiments, the placental preparation may further comprise one or more protease inhibitors. In some embodiments of said method, the one or more protease inhibitors may be added prior to gross homogenization. In some embodiments, the one or more protease inhibitors may be selected from the group comprising 4-(2-Aminoethyl) henzenesulfonyl fluoride hydrochloride (AEBSF), Bovine Lung Aprotinin, N-(trans-Epoxysuccinyl)-L-leucine 4-guanidinobutylamide, and Leupeptin. In some embodiments, the placental tissue may be the chorion. In some embodiments, the one or more protease inhibitors may be removed prior to administration of the placental preparation to said individual.

In an embodiment, the present invention relates to a method of making a placental preparation for treating an individual that may have a malady selected from the group comprising arthritis, wound healing, scar treatment, tissue growth, tissue healing, tissue matrix regeneration/repair, engraftment, inflammation, and conditions associated with modulating TGF-β signaling, wherein said method may comprise: procuring placental tissue and adding protease inhibitors to the placental tissue and then administering one or more of the following steps: (a) gross homogenization; (b) cell lysis; (c) separation of fluid from solid cell components; and (d) lyophilization and/or freeze to generate the placental preparation. In some embodiments, a filtration step may be performed after the separation and before the lyophilization step.

In some embodiments, the separation step may be performed by centrifugation. In some embodiments, the lyophilization step may be performed at reduced pressure. For example, the lyophilization step may be performed at 0.5 atmospheres or less, or 0.3 atmospheres or less, or 0.2 atmospheres or less, or 0.1 atmospheres or less, or 0.05 atmospheres or less, or 0.01 atmospheres or less, or 0.001 or less atmospheres. In some embodiments, the placental tissue may comprise a chorion. In some embodiments, the placental tissue may consist of the chorion.

Example 1

Placenta/amniotic membrane was procured and the human placental homogenate was isolated as follows. The placenta/amniotic membrane was procured from a contract hospital via a placenta donation. The donor was screened according to American Association of Tissue Banks (AATB) guidelines. The placenta/amniotic membrane was placed in 0.9% normal saline (NS, 154 mM NaCl, 308 mOsm/L). The placenta was removed from the 0.9% NS, the placental disc was separated from the amniotic membrane, chorion, and umbilical cord, and dissected into pieces approximately 1.5 inches by 2 inches. These smaller pieces of placental disc were placed in a container with approximately 400 mL of 1× phosphate buffered saline (PBS, 137 mM NaCl, 2.7 mM KCl, 4.3 mM $Na_2HPO_4$, 1.47 mM $KH_2PO_4$, pH 7.4). The container was placed on a shaking platform and shaken at 120 rpm for 12 to 24 hrs. The placental disc pieces were grossly homogenized using a laboratory blender with 1×PBS or 1×PBS that contained protease inhibitor (PI) at a 1× final concentration (AEBSF 500 uM, Aprotinin 150 nM, E-64 1 uM, Leupeptin 1 uM). The gross homogenate was placed into 250 mL containers and centrifuged for 10 minutes at 4,000 times gravity. The gross homogenate was poured into the container for a ratio of approximately 1:5, tissue volume: total volume. The container was vortexed/shaken to re-suspend the pellet. The suspension is centrifuged for 10 minutes at 4,000 times gravity. This wash procedure is repeated for a total of three washes. The mixture was not centrifuged after the last wash. The washes removed blood from the tissue. The contents of the 250 mL containers were diluted with either 1×PBS or IX PBS-1× PI to double the volume. The mixture was then placed into a reservoir feed connected to a high-pressure homogenizer. The homogenate was then placed into 250 mL containers and centrifuged at 15,000 times gravity for 10 minutes.

This procedure was performed on 6 placental discs. At the gross homogenization step, the placental discs were split into two groups, one group that was finished with 1×PBS and another that was finished with 1×PBS—1× PI.

A Bio-Plex MAGPIX Multiplex Reader (Bio-Rad Laboratories, Hercules, CA) was used to quantify the amounts of cytokines and growth factors present in the solution extracted from the placental disc. A Bio-Plex Pro Human Chemokine plane, 40-plex assay (Bio-Rad Laboratories, Hercules, CA) was obtained. The standards were diluted in appropriate diluent. Assay beads were diluted and 50 μL was added to each well of the 96-well plate and washed twice with assay buffer. The plate was placed on a magnetic plate holder and the solution removed from the wells. The standards, samples, and blanks were loaded into each respective well of the 96-well plate and incubated for 1 hour at room temperature (note: duplicate measurements were performed on each standard, sample and blank). The plate was washed by placing the plate on the magnetic plate holder, removing the solution, washing with wash buffer, and removing the wash buffer by placing the well plate on the magnetic plate holder. The detection antibodies were added to each well and incubated for 30 minutes at room temperature. The plate was washed 3 times with wash buffer and the streptavidin-PE indicator was added to each well. The plate was incubated for 10 minutes in the dark at room temperature. The plate was washed 3 times in assay buffer and measurements were taken on the MAGPIX multiplex reader. Data was analyzed on Bio-Plex reader software (Bio-Rad Laboratories, Hercules, CA) and a two-way ANOVA was utilized to compare the treatment groups.

Table 1 below shows data with the concentrations of proteins isolated from placenta in the presence and absence of protease inhibitors.

TABLE 1

| Protein | Concentration in the Presence of Protease Inhibitors (pg/mL) | Concentration in the Absence of Protease Inhibitors (pg/mL) |
|---|---|---|
| GCP-2 | 432.4 | 299.1 |
| IL-2 | 22.3 | 18.0 |
| IL-8 | 30,851.4 | 2423.7 |
| MCP-1 | 1854.5 | 449.8 |
| MIF | 478,523.1 | 336,076.8 |
| MIP-1α | 293.6 | 193.4 |
| MIP-3α | 58.2 | 27.6 |

The data in Table 1 shows that the addition of protease inhibitors increases the amount of the various proteins isolated from the placenta. Not intending to be bound by theory, the increased concentration of proteins likely increases the bioavailability of various proteins to aid in treating diseases and/or conditions.

Figure 2:
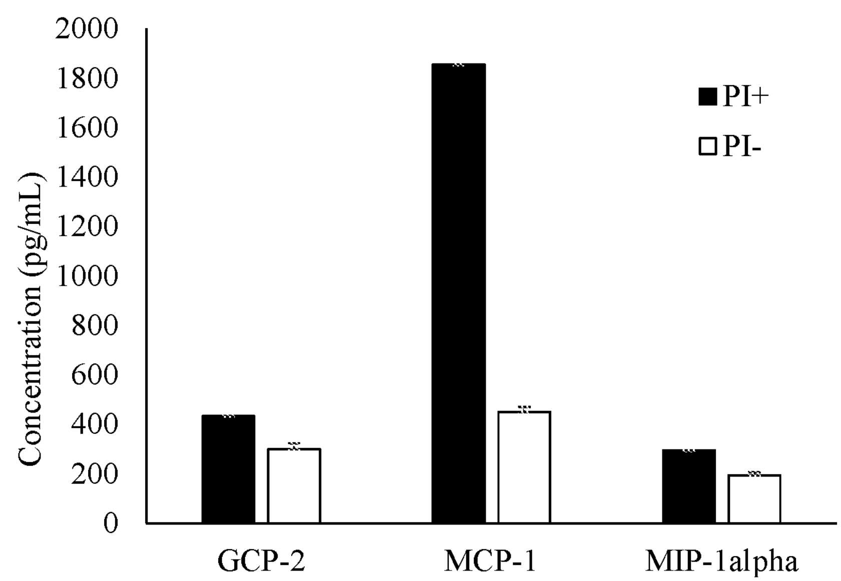
FIG. 2 shows the protein concentration amounts of granulocyte chemotactic protein 2, monocyte chemotactic protein 1, and macrophage inflammatory protein 1 from placental tissue in both the presence and absence of protease inhibitors.
Figure 3:
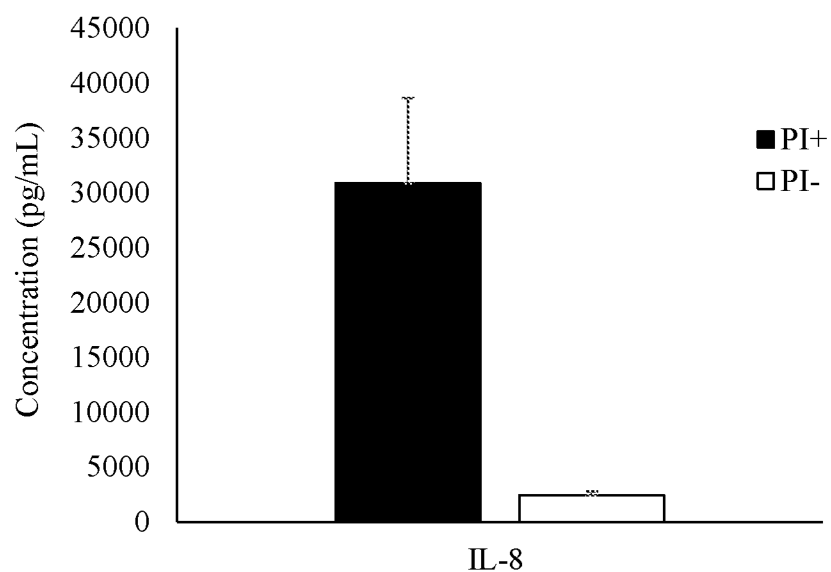
FIG. 3 shows the protein concentration amounts of interleukin 8 from placental tissue in both the presence and absence of protease inhibitors.
Figure 4:
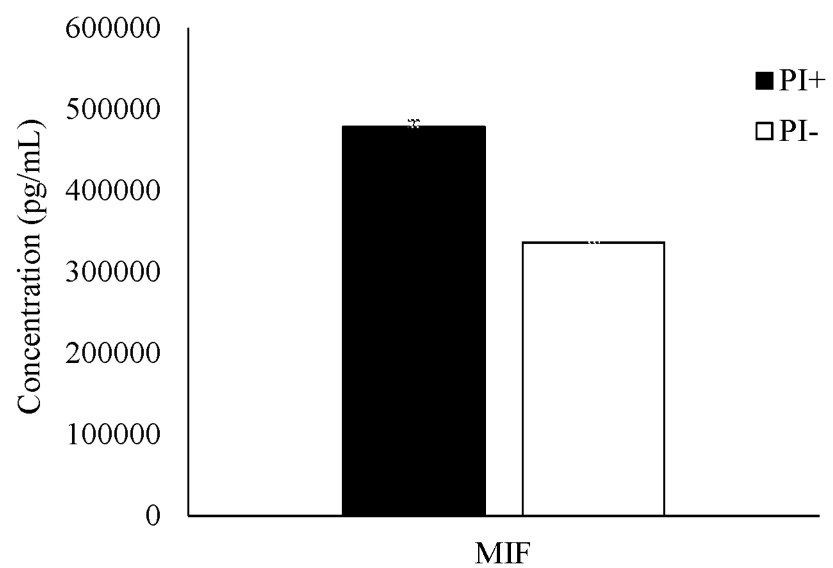
FIG. 4 shows the protein concentration amounts of macrophage inhibitory factor from placental tissue in both the presence and absence of protease inhibitors.

FIGS. 1-4 show the results of assays determining the amount of various amniotic proteins in the presence of protease inhibitors (dark bar) and absence of protease inhibitors (light bar) of protease inhibitors. FIG. 1 shows the isolated protein concentration amounts of interleukin 2 (IL-2) and macrophage inflammatory protein 3 (MIP-3α) from placental tissue. FIG. 2 shows the isolated protein concentration amounts of granulocyte chemotactic protein 2 (GCP-2), monocyte chemotactic protein 1 (MCP-1), and macrophage inflammatory protein 1 (MIP-1α) from placental tissue. FIG. 3 shows the isolated protein concentration amounts of interleukin 8 (IL-8) from placental tissue. FIG. 4 shows the isolated protein concentration amounts of macrophage inhibitory factor (MIF) from placental tissue. The compositions comprising protease inhibitors all showed a statistically significant increase in the isolated protein concentration as compared to those without protease inhibitors. The smallest increase was with IL-2, which produced a nearly 24% increase in IL-2 concentration in the composition comprising protease inhibitors, with a p-value less than 0.05 (FIG. 1). A similar increase in protein concentration was shown for MIF, GCP-2, and MIP-la, with each showing increases of 42-52% in compositions comprising protease inhibitors over those without protease inhibitors. The p-value for GCP-2 and MIP-la was less than 0.01; the p-value for MIF was less than 0.05 (FIG. 2 and FIG. 4). A significant increase in protein concentration was shown for MIP-3a and MCP-1 in the protease inhibited compositions with each more than doubling the protein concentration, with increases of 111% and 312%, respectively. The p-value for MIP-3a was less than 0.05; the p-value for MCP-1 was less than 0.01 (FIG. 1 and FIG. 2). A striking increase in protein concentration was shown for IL-8, with an increase of 1173% in the composition comprising protease inhibitors over that without protease inhibitors, with a p-value of less than 0.05 (FIG. 3).

Example 2

The following method is illustrative of one process of the invention that can be used to make the placental preparations of the present invention.

Step 1

The placenta/amniotic membrane is procured from a contract hospital by a placenta donation coordinator. The coordinator/QA department screens the donor according to AATB and company standards. The coordinator places the placenta/amniotic membrane in 0.9% normal saline (NS).

Step 2

Placenta is removed from the 0.9% NS and dissected into approximately 1.5 inch by 2 inch pieces. Smaller pieces are placed in container with approximately 400 mL of 1× phosphate buffered saline (PBS). The container is placed on a shaking platform shaken at 120 rpm for 12-24 hrs. Shaking the tissue in PBS removes gross amounts of blood from the tissue.

Step 3

Gross homogenization: Placenta pieces are grossly homogenized using a laboratory blender with 1×PBS that also contains protease inhibitor (P1) at a 1× final concentration. The protease inhibitor may be utilized to prevent the breakdown of proteins, specifically growth factors, chemokines, and cytokines present in the cells of the placenta.

Centrifugation: The gross homogenate is placed into 250 mL containers and centrifuged for 5 minutes at 10000× g. This step separates the bloody fluid from the blended tissue. The blended tissue may form a pellet at the bottom of the container. The bloody fluid is discarded.

Wash: 1×PBS with 1×PI is poured into the container for a ratio of ~1:5, tissue volume:total volume. The container is vortexed/shaken to re-suspend the pellet. The suspension is centrifuged for 5 minutes at 4000× g. This wash procedure is repeated for a total of three washes. The mixture is not centrifuged after the last wash. These washes remove blood from the tissue. The mixture is cooled to 4° C.

Step 4

Cell lysis is accomplished by one of the following procedures. Cell lysis may release chemokines, cytokines, and growth factors from the cells.

High Pressure Homogenization: The contents of the 250 mL containers are diluted with 1×PBS with 1×PI to double the volume. The mixture is then placed into cooled reservoir feed connected to a high-pressure homogenizer. The purpose of this step is to lyse any unlysed cells. The pressure and number of passes will be optimized by tests for chemokine and cytokine levels as well as bioactivity.

Freeze/Thaw: The contents of the 250 mL containers are poured into sterile bags and double sealed using a heat sealer. After sealing, the bags are placed on a tray in a −30° C. freezer. The number of bags varies based on total volume of gross homogenate mixture. The gross homogenate is poured into the bags to a volume that results in approximately 1-inch thick bags when laid on the tray. The bags of frozen gross homogenate are removed from the freezer and placed in a warm water bath 37.8° C. to 43.3° C. The homogenate is removed from the warm water bath as soon as it is thawed completely. The thawed mixture is poured into a container and blended using a handheld homogenizer on high speed. The blended mixture is placed into a sterile bag and sealed. This procedure is repeated for a total of up to 3 freeze/thaws.

Chemical Lysis: The gross homogenate is centrifuged and the supernatant is discarded. The pellet is washed with Bio-Rad cell wash buffer. The volume of cell wash buffer varies based on tissue volume. Two times the tissue volume of buffer is added. The pellet and buffer are vortexed/shaken to re-suspend the pellet. The mixture is centrifuged for 5 minutes at 10000×g. The supernatant is discarded. Bio-Rad cell lysis solution is added. The volume of cell lysis solution varies based on tissue volume. Two times the tissue volume of lysis solution is added. The pellet and lysing solution are vortexed/shaken to re-suspend the pellet. The mixture is placed in the refrigerator and allowed to sit for 5 minutes.

Centrifugation: After one of the above procedures is completed the homogenate is then placed into 250 mL containers and centrifuged at 15000×g for 10 minutes. This step separates the cellular debris from the fluid. The fluid should contain chemokines, cytokines, and growth factors. The supernatant is retained.

Step 5

Vacuum filtration: The supernatant from the above step is placed in a vacuum filtration system. The system contains two filters. The initial filter has a 1 μm pore size, which is followed by a filter with a 0.45 μm pore size. This step is to remove any remaining cellular debris and to clarify the supernatant. The filtrate is retained.

Step 6

HPH (human placental homogenate) Preparations—PH can be preserved in one of the following ways: (1) lyophilized and placed in sterile vials with testing to ensure bioactivity following lyophilization; (2) placed in sterile vials in liquid form for later use, for example, for injection; or (3) spray dried. HPH may be combined with other placental products, such as amnionic membrane. In one example, a-soaked amniotic membrane, the following process may be used.

Example 3—Wound Assay Using the Materials Generated in Example 1

A scratch assay, a standard in vitro assay of wound healing, was performed on 3 samples of both 1×PBS and 1×PBS-1×PI from the placental disc extraction. Human skin fibroblasts were cultured in Dulbecco's Modified Eagle's Medium (DMEM) with 10% fetal bovine serum in 12 well plates. When a monolayer was achieved, a cell scraper was used to remove a thin line of cells from the culture bottom. The wells were washed 3 times with Dulbecco's phosphate buffered saline (DPBS) to removed dissolved cells. Test articles were administered in serum-free DMEM at a volume approximately 10% of the total volume in each well. Plates were analyzed on ArrayScan ZTI per manufacturer instructions, with photomicrographs taken every 2 hours for the first 24 hours, then once at 48 and 72 hours.

Figure 5:
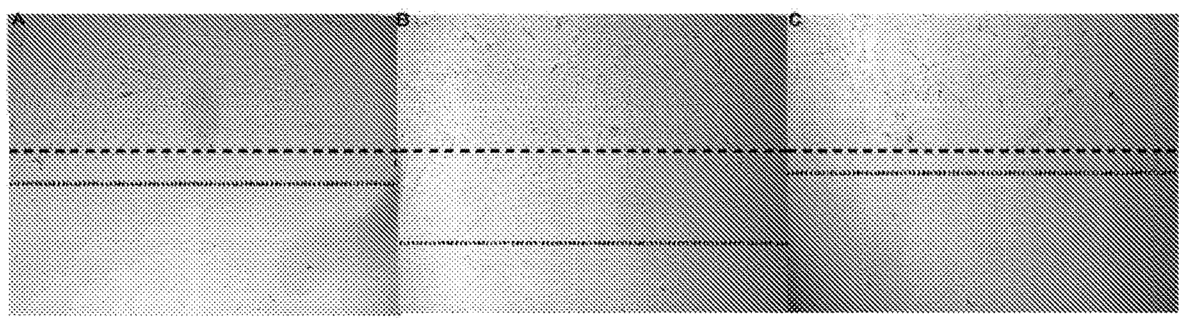
FIG. 5 shows the results of a wound healing assay using human placental homogenate (HPH) in the presence of a negative control with no serum (A), in the presence of serum that has been purified in the presence of protease inhibitors (B), and in the presence of serum that has been purified in the absence of protease inhibitors (C). As used herein, the terms purified and isolated are interchangeable.

FIG. 5 shows the results of a wound healing assay. A 24-hour In Vitro Wound Healing Assay was conducted where the Fibroblasts were treated with (A) negative control, normal growth media containing no serum, (B) 10% by volume of HPH solution processed with protease inhibitors in the media as described above, or (C) 10% by volume HPH solution processed without protease inhibitors in media described in A. The top line in the images represents the original line of wounding at time 0, while the bottom line indicates the furthest movement of cells into the wounded space. A greater distance is desirable for wound healing. Images are from 24 hours post-injury. The treatment of fibroblast with HPH processed with inhibitor (B) provided nearly twice the cell migration as the negative control (A). The negative control (A) was approximately equal to that of the HPH processed without inhibitors treatment (C).

Example 4

The placenta/amniotic membrane was procured from a contract hospital via a placenta donation. The donor was screened according to American Association of Tissue Banks (AATB). The placenta/amniotic membrane was placed in 0.9% normal saline (NS, 154 mM NaCl, 308 mOsm/L). The placenta was removed from the 0.9% NS, the placental disc was separated from the amniotic membrane, chorion, and umbilical cord, and dissected into approximately 1.5 inch by 2 inch pieces. These smaller pieces of placental disc were placed in a container with approximately 400 mL of 1× phosphate buffered saline (PBS, 137 mM NaCl, 2.7 mM KCl, 4.3 mM $Na_2HPO_4$, 1.47 mM $KH_2PO_4$, pH 7.4). The container was placed on a shaking platform shaken at 120 rpm for 12 to 24 hrs. The placental disc pieces were grossly homogenized using a laboratory blender with either 1×PBS or 1×PBS that contained protease inhibitor (PI) at a 1× final concentration (AEBSF 500 uM, Aprotinin 150 nM, E-64 1 uM, Leupeptin 1 uM). The gross homogenate was placed into 250 mL containers and centrifuged for 10 minutes at 4,000× gravity (g). The gross homogenate was poured into the container for a ratio of approximately 1:5, tissue volume: total volume. The container was vortexed/shaken to re-suspend the pellet. The suspension was centrifuged for 10 minutes at 4,000× g. This wash procedure was repeated for a total of three washes. The mixture was not centrifuged after the last wash. The washes remove blood from the tissue. The contents of the 250 mL containers were diluted with either 1×PBS or 1×PBS-1×PI to double the volume. The mixture was then placed into a reservoir feed connected to a high-pressure homogenizer. The homogenate was then placed into 250 mL containers and centrifuged at 15,000×g for 10 minutes. This procedure was performed on 6 donated placental discs.

The full term amniotic fluid was procured from a contract hospital via donation, where the donor was screened according to AATB standards. Fluid from 10 donors was collected for quantification of cytokines and growth factors.

A Bio-Plex MAGPIX Multiplex Reader (Bio-Rad Laboratories, Hercules, CA) was used to quantify the amounts of cytokines and growth factors present in the solution extracted from the placental disc. A Bio-Plex Pro Human Chemokine plane, 40-plex assay (Bio-Rad Laboratories, Hercules, CA) was obtained. The standards were diluted in appropriate diluent. Assay beads were diluted and 50 μL it was added to each well of the 96-well plate and washed twice with assay buffer. The plate was placed on a magnetic plate holder and the solution removed from the wells. The standards, samples and blanks were loaded into each respective well of the 96-well plate and incubated for 1 hour at room temperature (note: duplicate measurements were performed on each standard, sample and blank). The plate was washed by placing the plate on the magnetic plate holder, removing the solution, washing with wash buffer, and removing the wash buffer by placing the well plate on the magnetic plate holder. The detection antibodies were added to each well and incubated for 30 minutes at room temperature. The plate was washed 3 times with wash buffer and the streptavidin-PE indicator was added to each well. The plate was incubated for 10 minutes in the dark at room temperature. The plate was washed 3 times in assay buffer and measurements were taken on the MAGPIX multiplex reader. Data was analyzed on Bio-Plex reader software (Bio-Rad Laboratories, Hercules, CA) and a two-way ANOVA was utilized to compare the treatment groups.

The values of cytokines and growth factors from 16-20 week amniotic fluid were obtained from publications listed below:

1. Heikkinen J, Mottonen M, Pulkki K, Lassila O, Alanen A. Cytokine levels in midtrimester amniotic fluid in normal pregnancy and in the prediction of pre-eclampsia. *Scand J Immunol.* 2001; 53 (3):310-4.

2. Payne M S, Feng Z, Li S, Doherty D A, Xu B, Li J, Li L, Keelan J A, Zhou Y H, Dickinson J E, Hu Y, Newnham J P. Second trimester amniotic fluid cytokine concentrations, *Ureaplasma* sp colonization status and sexual activity as predictors of preterm birth in Chinese and Australian women. *BMC Pregnancy Childbirth.* 2014; 14:340.
3. Burns C, Hall S T, Smith R, Blackwell C. Cytokine levels in late pregnancy: Are female infants better protected against inflammation? *Front Immunol;* 6:318.

Figure 6:
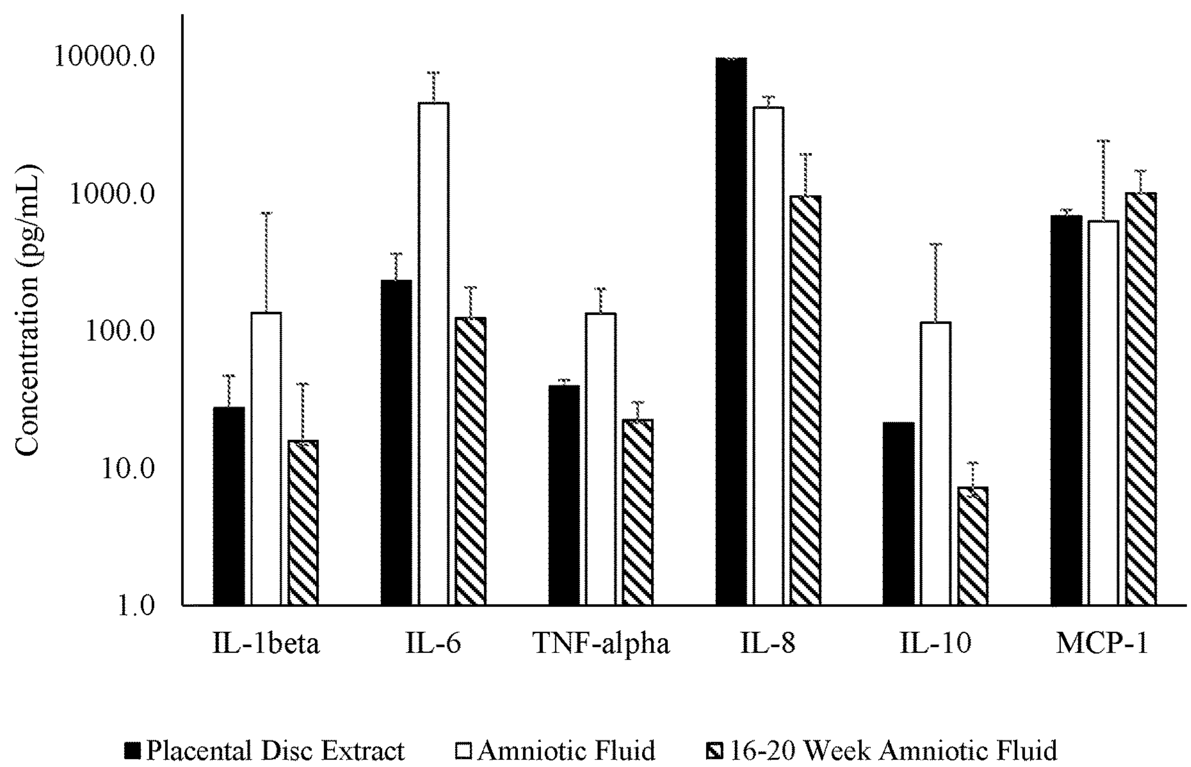
FIG. 6 shows the protein concentration amounts in placental composition with protease inhibitors, term amniotic fluid, and 16-20 week amniotic fluid.

Results from are shown in FIG. 6. The methods described produce a less variable product than that of the term amniotic fluid of 16-20 week amniotic fluid, as indicated by the lower standard deviation. The methods described produce a product that varies by 11 to 25%, whereas the quantities in the natural product (both amniotic fluids) can vary from 44 to over 100%. There is also a more favorable balance between the inflammatory and anti-inflammatory components of the product produced by the methods described. The inflammatory components, IL-1 beta, IL-6, and TNF-alpha, are much lower in the product produced by the described methods than those found in term amniotic fluid. There is a more favorable ratio of IL-6 to IL-10 in the product described by the method (10.8) then and in term amniotic fluid (34.5). There are higher quantities of anti-inflammatory components, IL-8 and MCP-1, in the product produced by the described method than those found in term amniotic fluid. Finally, the quantities of these proteins, IL-1 beta, IL-6, TNF-alpha, IL-8, IL-10, and MCP-1, in the product produced by the methods described is more similar to the quantities reported for 16-20 week amniotic fluid than term fluid.

The term "effective amount" as used herein, refers to a sufficient amount of an agent, a compound, or ingredients being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. An "effective amount" of a compound/ingredients disclosed herein, is an amount effective to achieve a desired pharmacologic effect or therapeutic improvement without undue adverse side effects. It is understood that "an effect amount" can vary from subject to subject, due to variation in metabolism of the composition, age, weight, general condition of the subject, the condition being treated, the severity of the condition being treated, and the judgment of the prescribing physician.

It is contemplated and therefore within the scope of the present invention that any feature that is described above can be combined with any other feature that is described above (even if those features are not described together). It should be understood that the present invention contemplates and it is therefore within the scope of the invention that any element that is described can be omitted from the compositions (except for those necessary to produce the desired utility of the invention) and/or methods of the present invention. When ranges are disclosed, it should be noted that any numeric point that fits within the scope of that range is contemplated as a new endpoint for a subrange. Moreover, it should be understood that the present invention contemplates minor modifications that can be made to the compounds, compositions and methods of the present invention. In any event, the present invention is defined by the below claims, which follow and the breadth of interpretation which the law allows.

What is claimed is:

1. A placenta-derived composition comprising an acellular extract of placental tissue and two or more exogenous protease inhibitors, wherein the two or more exogenous protease inhibitors comprise leupeptin and one or more protease inhibitors selected from the group consisting of 4-(2-Aminoethyl) benzensulfonyl fluoride hydrochloride (AEBSF), N-(trans-Epoxysuccinyl)-L-leucine 4-guanidinobutylamide, N-ethylmaleimide (NEM), ethylenediamine tetraacetic acid (EDTA), ethylene glycol-bis-(2-aminoethyl (ether) NNN'N'-tetraacetic acid) (EGTA), ammonium chloride, boceprevir, danoprevir, narlaprevir, telaprevir, and vaniprevir, wherein the placental tissue comprises a placental disc.

2. The placenta-derived composition of claim 1, wherein the two or more exogenous protease inhibitors comprise leupeptin and 4-(2-Aminoethyl) benzenesulfonyl fluoride hydrochloride (AEBSF).

3. The placenta-derived composition of claim 1, wherein the composition comprises a higher concentration amount of interleukins relative to a placenta-derived composition comprising an acellular extract of placental tissue comprising a placental disc that is prepared in the absence of exogenous protease inhibitors.

4. A placenta-derived composition comprising an acellular extract of placental tissue and an exogenous protease inhibitor consisting of leupeptin and AEBSF, wherein the placental tissue comprises a placental disc.

5. The placenta-derived composition of claim 4, wherein the composition comprises a higher concentration amount of interleukins relative to a placenta-derived composition comprising an acellular extract of placental tissue comprising a placental disc that is prepared in the absence of exogenous protease inhibitors.

6. A placenta-derived composition comprising an acellular extract of placental tissue and an exogenous protease inhibitor consisting of leupeptin or AEBSF, wherein the placental tissue comprises a placental disc.

7. The placenta-derived composition of claim 6, wherein the composition comprises a higher concentration amount of interleukins relative to a placenta-derived composition comprising an acellular extract of placental tissue comprising a placental disc that is prepared in the absence of exogenous protease inhibitors.

8. An acellular placental preparation extracted from placental tissue, the acellular placental preparation comprising two or more exogenous protease inhibitors, wherein the two or more exogenous protease inhibitors comprise leupeptin and one or more protease inhibitors selected from the group consisting of 4-(2-Aminoethyl) benzensulfonyl fluoride hydrochloride (AEBSF), N-(trans-Epoxysuccinyl)-L-leucine 4-guanidinobutylamide, N-ethylmaleimide (NEM), ethylenediamine tetraacetic acid (EDTA), ethylene glycol-bis-(2-aminoethyl/(ether)NNN'N'-tetraacetic acid) (EGTA), ammonium chloride, boceprevir, danoprevir, narlaprevir, telaprevir, or vaniprevir, wherein the placental tissue comprises a placental disc and wherein said preparation is produced by a process comprising:

adding the two or more exogenous protease inhibitors to the placental tissue;

homogenization of the placental tissue;

cell lysis to generate a solid cellular debris and an acellular fluid;

separation of the acellular fluid from the solid cellular debris; and lyophilization and/or freezing of the acellular fluid.

9. The acellular placental preparation of claim 8, wherein the process further comprises filtering the acellular fluid after the separation and before the lyophilization steps.

10. The acellular placental preparation of claim 8, wherein the two or more exogenous protease inhibitors are added prior to homogenization.

11. The acellular placental preparation of claim 8, wherein the two or more exogenous protease inhibitors comprise leupeptin and 4-(2-Aminoethyl) benzenesulfonyl fluoride hydrochloride (AEBSF).

12. The placenta-derived composition of claim 8, wherein the two or more exogenous protease inhibitors consist of leupeptin and AEBSF.

13. The acellular placental preparation of claim 8, wherein the separation of the acellular fluid from the solid cellular debris comprises centrifugation.

14. The acellular placental preparation of claim 8, further comprising one or more diluents, excipients, and/or carriers.

15. The acellular placental preparation of claim 8, wherein the acellular placental preparation comprises a higher concentration amount of interleukins relative to an acellular placental preparation comprising a placental tissue comprising a placental disc that is prepared in the absence of exogenous protease inhibitors.

16. The acellular placental preparation of claim 8, wherein the exogenous protease inhibitors that are added to the placental tissue during the process are not removed from the acellular placental preparation.

17. A method of making a placental product comprising two or more exogenous protease inhibitors, comprising:

adding the two or more exogenous protease inhibitors to a placental tissue comprising a placental disc, wherein the two or more exogenous protease inhibitors comprise leupeptin and one or more protease inhibitors selected from the group consisting of 4-(2-Aminoethyl) benzensulfonyl fluoride hydrochloride (AEBSF), N-(trans-Epoxysuccinyl)-L-leucine 4-guanidinobutylamide, N-ethylmaleimide (NEM), EDTA, EGTA, ammonium chloride, boceprevir, danoprevir, narlaprevir, telaprevir, and vaniprevir;

homogenizing the placental tissue;

lysing the placental tissue to generate a solid cellular debris and an acellular fluid;

separating the acellular fluid from the solid cellular debris; and lyophilizing and/or freezing the acellular fluid.

18. The method of claim 17, further comprising filtering the acellular fluid.

19. A method of treating an individual comprising administering the placental preparation of claim 8 to the individual.

* * * * *